United States Patent [19]

Becker et al.

[11] Patent Number: 4,608,069
[45] Date of Patent: Aug. 26, 1986

[54] SEPARATION OF HIGHER BOILING IMPURITIES FROM LIQUEFIED GASES

[75] Inventors: Hans Becker, Munich; Herwig Landes, Ingolstadt, both of Fed. Rep. of Germany

[73] Assignee: Linde Aktiengesellschaft, Wiesbaden, Fed. Rep. of Germany

[21] Appl. No.: 710,808

[22] Filed: Mar. 12, 1985

[30] Foreign Application Priority Data

Mar. 12, 1984 [DE] Fed. Rep. of Germany ....... 3408997

[51] Int. Cl.⁴ .............................................. F25J 3/02
[52] U.S. Cl. .......................................... 62/26; 62/30; 62/31; 62/34
[58] Field of Search .................. 62/23, 24, 31, 32, 34, 62/36, 42, 25, 26, 29, 30

[56] References Cited

U.S. PATENT DOCUMENTS 4,478,621  10/1984  Fabian ..................................... 62/39

Primary Examiner—Frank Sever
Attorney, Agent, or Firm—Millen & White

[57] ABSTRACT

For separating a higher boiling component from a liquefied gas, e.g., CO, rectification is used wherein a partial stream of the liquefied gas is vaporized, superheated, and then fed into the lower portion of a rectification column. The remainder of the liquefied gas in the liquid phase is fed into the upper portion of the rectification column. The rectification results in the higher boiling component being concentrated in the bottoms, and the overhead gas product being purified thereby. Additional purification is possible by liquefying and refluxing part of the overhead gas product, and in this case, it is possible to superheat the entire liquefied gas so as to obtain ultra high purity product.

22 Claims, 2 Drawing Figures

4,608,069

SEPARATION OF HIGHER BOILING IMPURITIES FROM LIQUEFIED GASES

BACKGROUND OF THE INVENTION

This invention relates to a distillation process particularly to the separation of higher boiling impurities from liquefied gases by rectification, and associated apparatus.

Various condensation processes are used advantageously to separate gaseous components from raw gases, for example to obtain CO from steam reformer gases. Gases produced by a condensation process frequently contain trace amounts of light (lower boiling) and heavy (higher boiling) components which are detrimental to certain uses of the liquefied gases, e.g., downstream synthesis operations. The light components can be separated simply and economically, for example, by stepwise condensation and expansion, as has been described, for example, in published German application No. P 33 13 171.6 (corresponding to assignee's U.S. application Ser. No. 600,059, filed Apr. 12, 1984) for the separation of an $H_2$-CO mixture. In contrast, the separation of heavy components generally requires a relatively high expenditure in energy as well as apparatus.

SUMMARY OF THE INVENTION

Therefore, an object of the present invention is to provide an improved process and associated apparatus for the separation of heavy components, especially in a system which is relatively simple and cost-effective.

Upon further study of the specification and appended claims, further objects and advantages of this invention will become apparent to those skilled in the art.

To attain these objects, there is provided a process for separating a higher boiling component from a liquefied gas by rectification, comprising vaporizing a partial stream of the liquefied gas, superheating the resultant vapor and introducing the resultant superheated vapor into the lower portion of a rectification column, passing the remainder of the liquefied gas in the liquid phase into the upper portion of the rectification column, and conducting rectification so as to withdraw said higher boiling component as bottoms and to recover vaporized liquefied gas depleted in said higher boiling component, as overhead gas product.

An essential feature of this invention is that the superheating of at least a partial stream of the column feed replaces the sump heater or reboiler, including, of course, the specifically designed heat exchanger used for this purpose. Moreover, the process of this invention can be frequently performed without any additional energy input. In this connection, the losses of overhead gas removed with the withdrawn higher boiling component depends on the degree of superheating, the more the superheating the lower the losses. Generally, the superheating is about to 3° to 100° K., especially about 5° to 50° K. above saturated conditions.

Whereas by the above described invention, the content of heavy components in the liquified gas product can be lowered, the extent of purification is limited by the content of the heavy components in the raw gas and by the gas/liquid equilibrium at the head of the column. To overcome this limitation whenever desired, a more sophisticated and improved aspect of this invention comprises heating, compressing and liquefying a partial stream of said overhead product gas and returning via a pressure reduction zone resultant liquefied partial stream of gas overhead as reflux into the upper portion of the rectification column. By the recycling of a partial product stream, any desired purity can be achieved, since heavier components are retained in the column and withdrawn as bottoms. For this purpose, the reflux is advantageously introduced into the rectification column above the feed point for the liquid phase liquefied gas, thereby providing the column with an enriching section as well as a stripping section.

To lower the operating and investment costs, an additional improvement comprises vaporizing and superheating the liquefied gas in indirect heat exchange relationship with gas to be liquefied. Moreover, it is advantageous to conduct the liquefaction of the partial product stream of overhead product in heat exchange against the overhead product gas to be heated as well as the bottoms product.

The process of this invention is usable with special advantage for the separation of minor contents, e.g., not more than about 5 mol-%, of heavy components from liquefied gases. For example, small amounts of about 1 mol-% of methane as well as optionally other heavy components generally in even lower amounts, such as, for example, ethane, can be advantageously separated from liquefied CO. In the context of the invention, liquefied gases refer to gases having a normal boiling point below 400° K., especially below 350° K.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein.

Figure 1:
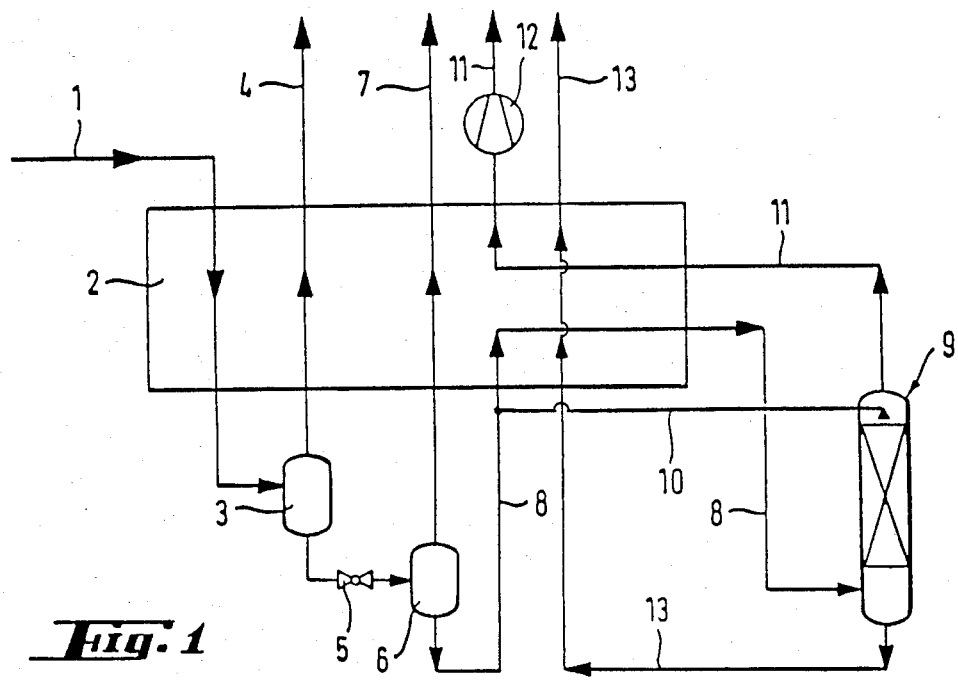
FIG. 1 depicts a preferred embodiment of the process based on CO as the liquefied gas and without reflux.

According to FIG. 1, crude gas from a prepurification stage is supplied via a conduit 1 at a temperature of 283° K. under a pressure of 9 bar. The crude gas has the following composition, in mol-%:

| | |
|---|---|
| $H_2$ | 32.52 |
| $N_2$ | 0.01 |
| CO | 67.41 |
| $CH_4$ | 0.06 |

In a heat exchanger 2, the crude gas is cooled to 80.5° K., thus condensing the predominant portion of the CO, the latter being separated in a separator 3. The remaining gaseous fraction, $H_2$ with about 11.6 mol-% CO and 7 ppm methane, is heated in heat exchanger 2 and discharged via conduit 4. The liquid from separator 3 is expanded in a valve 5 to a pressure of about 1.5 bar. During this step, dissolved $H_2$ is separated in the gaseous phase in a separator 6, this $H_2$ being likewise heated in heat exchanger 2 and then removed via conduit 7 as recycle medium or as fuel gas.

The liquefied gas withdrawn from separator 6 has a temperature of about 79° K. and the following composition (mol-%):

| | |
|---|---|
| $H_2$ | 0.14 |
| $N_2$ | 0.01 |

| | |
|---|---|
| CO | 99.75 |
| CH₄ | 0.10 |

A partial stream of the liquefied gas, for example 85%, is vaporized in heat exchanger 2, superheated by about 25° K., and introduced into the lower portion of a rectification column 9. The other partial stream of the liquefied gas is conducted in the liquid phase via conduit 10 to the head of the rectification column 9. The super-heating of the partial stream in conduit 8 replaces the reboiler or sump heating for the rectifying column, so that purified CO product can be withdrawn overhead via conduit 11, said CO product containing only about 70 ppm of methane. After being heated in heat exchanger 2 to 279° K. and compressed in compressor 12, to 5 bar, the purified CO is discharged. A fraction rich in methane is withdrawn from the sump of the rectification column 9 by way of conduit 13, heated in heat exchanger 2 to 279° K., and discharged.

Figure 2:
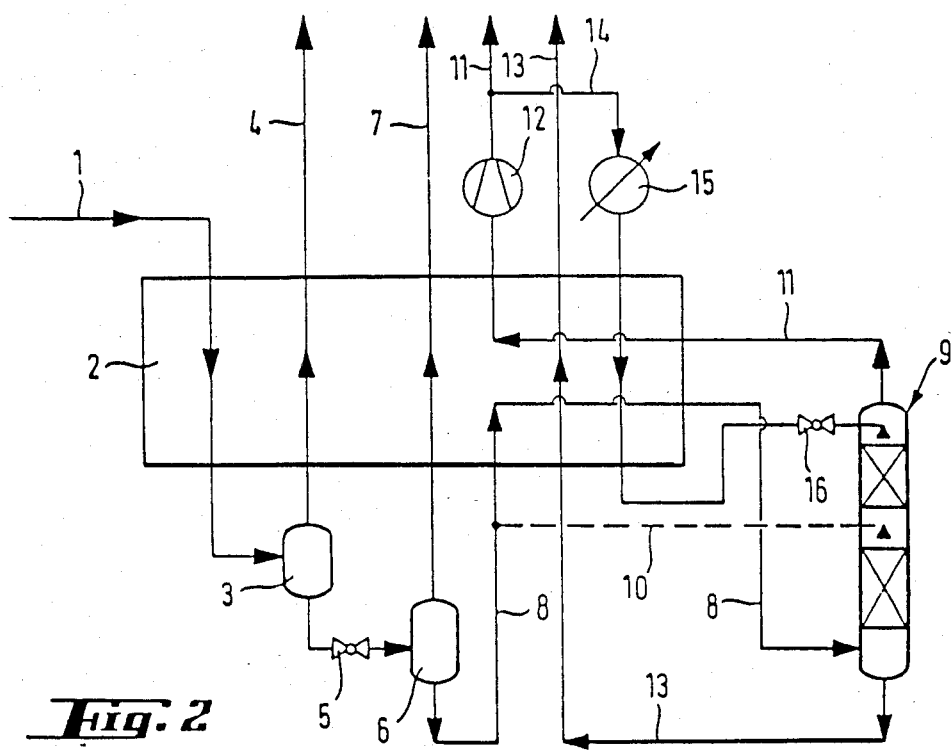
FIG. 2 depicts the same embodiment with reflux.

However, by operating the process in the above described manner, only a limited $CH_4$ purity can be obtained in the CO product. To provide any desired $CH_4$ purity, the process is modified as illustrated in FIG. 2. The same components are denoted by identical reference numerals as in FIG. 1.

In contrast to the mode of operating the process according to FIG. 1, a partial stream, for example 15%, of the heated and compressed CO product is here recycled via conduit 14, the heat of compression is removed in a cooler 15, further cooling to 80.5° K. is effected in heat exchanger 2, and finally the cold product is expanded in a valve 16 to 1.3 bar and introduced in the liquid phase as reflux at the head of the rectifying column 9. The reflux is introduced, in this case, above the feed point for the liquefied gas from the conduit 10 (shown in dashed lines) into the rectification column. In this version of the process, there is the possibility of vaporizing and super-heating the entire liquefied gas from separator 6. However, a somewhat higher energy requirements exists, owing to the compression energy required for the reflux. In a CO product obtained in this way, there are, if this is necessary, no longer any measurable traces of methane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. When "high boiling component" is mentioned in the claims, it is intended to cover one or more molecular entities.

What is claimed:

1. A process for a low temperature separation of a higher boiling component from a liquefied gas by rectification, comprising vaporizing a partial stream of the liquefied gas, providing a heat exchanger specifically designed to enable replacement of the sump heater or reboiler of the column by super-heating the resultant vapor in said heat exchanger and introducing the resultant superheated vapor into the lower portion of a rectification column, passing the remainder of the liquefied gas in the liquid phase into the upper portion of the rectification column, and conducting rectification so as to withdraw said higher boiling component as bottoms and to recover vaporized liquefied gas depleted in said higher boiling component, as overhead gas product.

2. A process according to claim 1, further comprising vaporizing and super-heating the liquefied gas in indirect heat exchanger relationship with gas to be liquefied.

3. A process according to claim 2 further comprising heating, compressing and liquefying a partial stream of said overhead product gas and returning via a pressure reduction zone resultant liquefied partial stream of gas overhead as reflux into the upper portion of the rectification column.

4. A process according to claim 3, said reflux being introduced into the rectification column above the feed point of the liquid phase liquefied gas.

5. A process according to claim 4 wherein the liquefied gas is CO and the higher boiling component comprises methane.

6. A process according to claim 3 further comprising liquefying said compressed partial stream of overhead product in indirect heat exchange relationship with the overhead product gas to be heated and with the bottoms product.

7. A process according to claim 6 wherein the liquefied gas is CO and the higher boiling component comprises methane.

8. A process according to claim 3 wherein the liquefied gas is CO and the higher boiling component comprises methane.

9. A process according to claim 2 wherein the liquefied gas is CO and the higher boiling component comprises methane.

10. A process according to claim 9 wherein the higher boiling component amounts to less than about one volume percent.

11. A process according to claim 1 further comprising heating, compressing and liquefying a partial stream of said overhead product gas and returning via a pressure reduction zone resultant liquefied partial stream of gas overhead as reflux into the upper portion of the rectification column.

12. A process according to claim 11, said reflux being introduced into the rectification column above the feed point of the liquid phase liquefied gas.

13. A process according to claim 12 wherein the liquefied gas is CO and the higher boiling component comprises methane.

14. A process according to claim 11 further comprising liquefying said compressed partial stream of overhead product in indirect heat exchange relationship with the overhead product gas to be heated and with the bottoms product.

15. A process according to claim 14 wherein the liquefied gas is CO and the higher boiling component comprises methane.

16. A process according to claim 11 wherein the liquefied gas is CO and the higher boiling component comprises methane.

17. A process according to claim 16 wherein the higher boiling component amounts to less than about one volume percent.

18. A process according to claim 1 wherein the liquefied gas is CO and the higher boiling component comprises methane.

19. A process according to claim 18 wherein the higher boiling component amounts to less than about one volume percent.

20. A process as claimed in claim 1, wherein the higher boiling component to be separated comprises less than 5 mol % of the liquified gas.

21. A process as claimed in claim 1, wherein liquified gas refers to a gas having a boiling point below 400° K. at atmospheric pressure.

22. A process for a low temperature separation of a higher boiling component from a liquefied gas by rectification, comprising completely vaporizing the liquefied gas, providing a heat exchanger specifically designed to enable replacement of the sump heater or reboiler of the column by super-heating the resultant vapor in said heat exchanger and introducing the resultant superheated vapor into the lower portion of a rectification column, conducting rectification so as to withdraw said higher boiling component as bottoms and to recover vaporized liquefied gas depleted in said higher boiling component, as overhead gas product, compressing and liquefying a partial stream of said overhead product gas and returning via a pressure reduction zone resultant liquefied partial stream of gas overhead as reflux into the upper portion of the rectification column.

* * * * *